(12) United States Patent
Goldstein et al.

(10) Patent No.: US 6,541,495 B1
(45) Date of Patent: Apr. 1, 2003

(54) CARBOXYLIC ACID DERIVATIVES AS INHIBITORS OF HYPERPROLIFERATION DISEASES

(75) Inventors: Steven W. Goldstein, Noank, CT (US); Kelly P. Longo, Mystic, CT (US); Bernard Hulin, Essex, CT (US)

(73) Assignee: Pfizer INC, New York, NY (US)

( * ) Notice: Subject to any disclaimer, the term of this patent is extended or adjusted under 35 U.S.C. 154(b) by 0 days.

(21) Appl. No.: 09/548,937

(22) Filed: Apr. 13, 2000

Related U.S. Application Data

(60) Provisional application No. 60/151,138, filed on Aug. 27, 1999.

(51) Int. Cl.$^7$ ................................................. A61K 31/42
(52) U.S. Cl. ........................................................ 514/374
(58) Field of Search .......................................... 514/374

(56) References Cited

U.S. PATENT DOCUMENTS 5,089,514 A   2/1992  Hulin .......................... 514/374

OTHER PUBLICATIONS

B. Hulin, J. Med. Chem., 1996, vol. 39: 3897–3907.

*Primary Examiner*—Jerome D. Goldberg
(74) *Attorney, Agent, or Firm*—Peter C. Richardson; Paul H. Ginsburg; Krishna G. Banerjee

(57) ABSTRACT

A method of treating hyperproliferation diseases in mammals in need of such treatment, which method includes administering to said mammal a therapeutically effective amount of a compound of the formula:

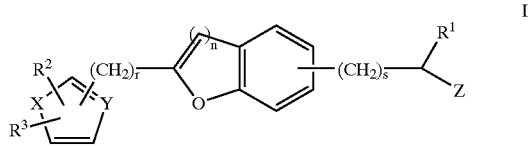

or a pharmaceutically acceptable salt, hydrate or prodrug thereof, wherein $R^1$, $R^2$, $R^3$, $R^4$, W, X, Y, Z and t are as defined herein.

6 Claims, No Drawings

CARBOXYLIC ACID DERIVATIVES AS INHIBITORS OF HYPERPROLIFERATION DISEASES

This application is based upon co-pending provisional application No. 60/151,138 filed Aug. 27, 1999.

BACKGROUND OF THE INVENTION

This invention relates to the treatment of hyperproliferative diseases, such as cancers, in mammals using substituted carboxylic acid derivatives, and substituted derivatives of other acids, of formula I, as defined below. The compounds of formula I are described in *J. Med. Chem.*, 1996, 39, 3897–3907 and U.S. Pat. No. 5,089,514, which issued Feb. 18, 1992, both of which are incorporated herein by reference in their entirety. These references describe compounds of formula I, specifically the substituted carboxylic acid derivatives of formula I, as hypoglycemic agents useful in the treatment of diabetes and related disorders.

A cell may become cancerous by virtue of the transformation of a portion of its DNA into an oncogene (i.e. a gene that upon activation leads to the formation of malignant tumor cells). Many oncogenes encode proteins that are aberrant tyrosine kinases capable of causing cell transformation. Alternatively, the overexpression of a normal proto-oncogenic tyrosine kinase may also result in proliferative disorders, sometimes resulting in a malignant phenotype. It has been shown that certain tyrosine kinases may be mutated or overexpressed in many human cancers such as brain, lung, squamous cell, bladder, gastric, breast, head and neck, oesophageal, gynecological and thyroid cancers. Furthermore, the overexpression of a ligand for a tyrosine kinase receptor may result in an increase in the activation state of the receptor, resulting in proliferation of the tumor cells or endothelial cells. Thus, it is believed that the growth of mammalian cancer cells can be selectively inhibited by reducing tyrosine kinase activity.

Polypeptide growth factors, such as vascular endothelial growth factor (VEGF) having a high affinity to the human kinase insert-domain-containing receptor (KDR) or the murine fetal liver kinase 1 (FLK-1) receptor, have been associated with the proliferation of endothelial cells and more particularly vasculogenesis and angiogenesis. See PCT international application publication number WO 95/21613 (published Aug. 17, 1995). A significant body of evidence has been put forth detailing the importance of VEGF in the formation of new blood vessels (angiogenesis). It has also been noted that new blood vessel formation is crucial in supplying and maintaining the physiological conditions and nutrients necessary for tumor growth and metastasis. It has been shown that both VEGF receptor subtypes appear to be over expressed in proliferating endothelial cells located in near proximity to tumor cells in vivo. At the molecular level, intracellular portions of both FLT-1 and FLK-1 contain functional tyrosine kinase domains. Kinase activities depend on high affinity to, and interaction with, VEGF. Such interaction results in the autophosphorylation of the receptors and ultimately in endothelial cell proliferation. High affinity VEGF binding and the resulting functional effects appear to depend on the presence of specific heparin sulfate proteoglycans (VEGF glyceptor) associated with the extracellular matrix of endothelial cells. This supposition is supported by the ability of exogenous levels of heparin to inhibit VEGF induced endothelial cell proliferation by acting as a sink for secreted VEGF. By inhibiting the binding of VEGF to VEGF glyceptor (GAG), phosphorylation of tyrosine (kinase) is modulated. Agents, such as the compounds of the present invention, which are capable of modulating the KDR/FLK-1 receptor, may be used to treat disorders related to vasculogenesis or angiogenesis. Such disorders include, but are not limited to, diabetes, diabetic retinopathy, hemangioma, glioma, melanoma, Kaposi's sarcoma and ovarian, breast, lung, pancreatic, prostate, colon and epidermoid cancer.

SUMMARY OF THE INVENTION

The present invention is directed to a method of treating hyperproliferation diseases in mammals in need of such treatment, comprising administering to said mammal a therapeutically effective amount of a compound of the formula:

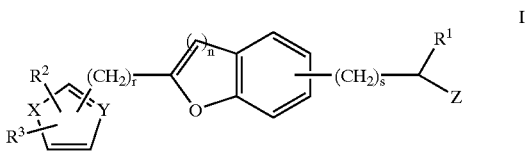

or a pharmaceutically acceptable salt, hydrate or prodrug thereof, wherein:

$R^1$ is a group having an acidic proton, particularly —$COY^1$ wherein $Y^1$ is hydroxy, ($C_1$–$C_3$)alkoxy, phenoxy, benzyloxy, amino, ($C_1$–$C_4$)alkanoylamino, ($C_1$–$C_4$)alkanesulfonylamino, benzenesulfonylamino, naphthalenesulfonylamino, di[($C_1$–$C_4$)]aminosulfonylamino or one of the foregoing groups mono- or disubstituted with ($C_1$–$C_3$)alkyl, trifluoromethyl, hydroxy, ($C_1$–$C_3$)alkoxy, fluoro or chloro, or $R^1$ is —$SO_2H$, —$PO_3H_2$,

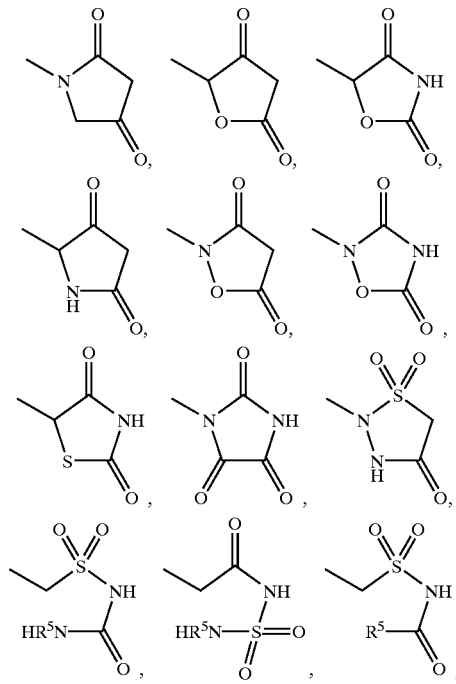

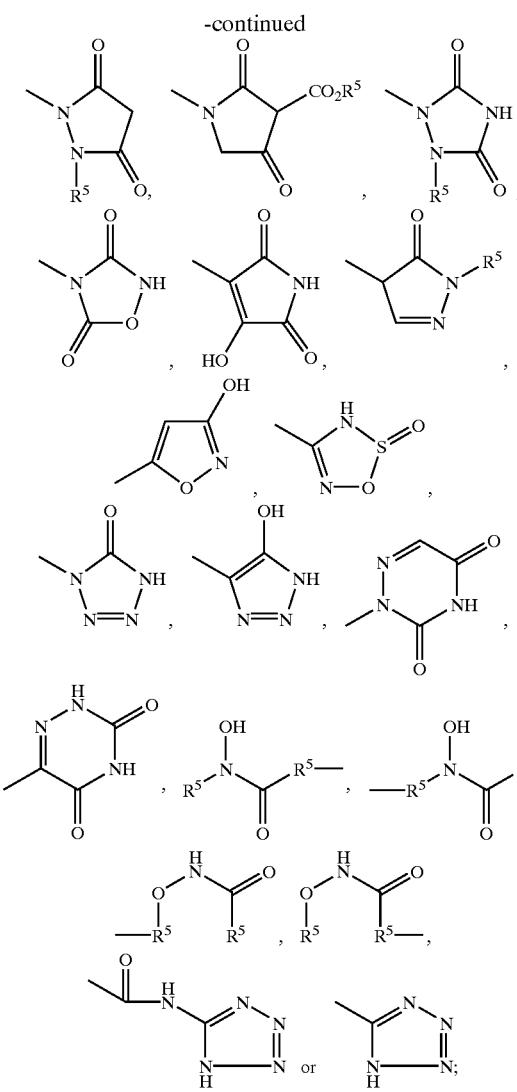

$R^2$ and $R^3$ are independently selected from hydrogen, $(C_1-C_{10})$alkyl, phenyl, and a 4 to 10 membered heterocyclic group, which is optionally substituted by one or more $R^4$ groups;

$R^4$ is thienyl, pyridyl, furyl, or pyrimidyl, halogen, $(C_1-C_6)$alkyl optionally substituted with from one to three fluorine atoms, $(C_1-C_6)$alkoxy, optionally substituted with from one to three fluorine atoms, $(C_3-C_{10})$ aryl, phenyl, $-(CH_2)_t$ phenyl, $-(CH_2)_t-(4$ to 10 membered heterocyclic group), nitro, cyano, amino, $-NH(C_1-C_6)$alkyl, $-N((C_1-C_8)$alkyl$)_2$, $-S(C_1-C_8)$ alkyl, $-SO(C_1-C_8)$alkyl, $-C(O)(C_1-C_8)$alkyl, $-CO(O)(C_1-C_8)$alkyl, wherein said phenyl, aryl or heterocyclic moiety may be optionally substituted with one or two substituents independently selected from halogen, $(C_1-C_6)$alkyl, $(C_1-C_6)$alkoxy, nitro, cyano, amino and trifluoromethyl;

$R^5$ is H, $C_1-C_{10}$ alkyl, $C_2-C_{10}$ alkenyl, $C_2-C_{10}$ alkynyl, $-(CH_2)_t(C_6-C_{10}$ aryl), or $-(CH_2)_t(4$ to 10 membered heterocyclic group), wherein t is an integer from 0 to 5; said alkyl group optionally including 1 or 2 hetero moieties selected from O, S and $-N(R^6)-$ with the proviso that two O atoms, two S atoms, or an O and S atom are not attached directly to each other; said aryl and heterocyclic $R^5$ groups being optionally fused to a $C_6-C_{10}$ aryl group, a $C_5-C_8$ saturated cyclic group, or a 4 to 10 membered heterocyclic group; one or two carbon atoms in said 4 to 10 membered heterocyclic group of $R^5$ being optionally substituted by an oxo (=O) moiety; $R^5$ groups being optionally substituted by one to five $R^7$ groups;

$R^6$ is H, $(C_1-C_8)$alkyl, $(C_3-CB)$cycloalkyl, or a 4 to 10 membered heterocyclic group optionally substituted with $(C_1-C_3)$alkyl;

$R^7$ is each independently selected from $C_1-C_{10}$ alkyl, $C_2-C_{10}$alkenyl, $C_2-C_{10}$alkynyl, halo, cyano, nitro, trifluoromethyl, trifluoromethoxy, azido, $-OR^8$, $-C(O)R^9$, $-C(O)OR^8$, $-NR^8C(O)OR^9$, $-OC(O)R^9$, $-NR^9SO_2R^8$, $-SO_2NR^8R^9$, $-NR^9C(O)R^8$, $-C(O)NR^8R^9$, $-NR^8R^9$, $-S(O)_jR^{10}$, $-SO_3H$, $-NR^8(CR^9R^{10})_tOR^9$, $-(CH_2)_t(C_6-C_{10}$ aryl), $-SO_2(CH_2)_t(C_6-C_{10}$aryl), $-S(CH_2)_t(C_6-C_{10}$aryl), $-O(CH_2)_t(C_6-C_{10}$aryl), $-(CH_2)_t(4$ to 10 membered heterocyclic group), and $-(CR^9R^{10})_mOR^9$, said alkyl group optionally containing one or two hetero moieties selected from O, S and $-N(R^8)-$ with the proviso that two O atoms, two S atoms, or an O and S atom are not attached directly to each other; aryl and heterocyclic moieties of $R^7$ being optionally fused to a $C_6-C_{10}$ aryl group, a $C_5-C_8$ saturated cyclic group, or a 4 to 10 membered heterocyclic group; one or two carbon atoms of the heterocyclic moieties of $R^7$ being optionally substituted by an oxo (=O) moiety; and the alkyl, aryl and heterocyclic moieties of $R^7$ groups being optionally substituted by one to three substituents independently selected from halo, cyano, nitro, trifluoromethyl, trifluoromethoxy, azido, $-NR^9SO_2R^8$, $-SO_2NR^8R^9$, $-C(O)R^8$, $-C(O)OR^8$, $-OC(O)R^8$, $-NR^9C(O)R^8$, $-C(O)NR^8R^9$, $-NR^8R^9$, $-(CR^9R^{10})_mOR^9$, $-OR^8$ and $R^8$;

$R^8$ is each independently selected from H, $C_1-C_{10}$ alkyl, $-(CH_2)_t(C_6-C_{10}$ aryl), and $-(CH_2)_t(4$ to 10 membered heterocyclic), said alkyl group optionally including one or two hetero moieties selected from O, S and $-N(R^6)-$ with the proviso that two O atoms, two S atoms, or an O and S atom are not attached directly to each other; said aryl and heterocyclic $R^8$ groups being optionally fused to a $C_6-C_{10}$ aryl group, a $C_5-C_8$ saturated cyclic group, or a 4 to 10 membered heterocyclic group; the foregoing moieties of $R^8$, with the exception of H, being optionally substituted by one to three substituents independently selected from halo, cyano, nitro, trifluoromethyl, trifluoromethoxy, azido, $-C(O)R^9$, $-C(O)OR^9$, $-CO(O)R^9$, $-NR^9C(O)R^{10}$, $-C(O)NR^9R^{10}$, $-NR^9R^{10}$, hydroxy, $C_1-C_6$ alkyl, and $C_1-C_6$ alkoxy;

$R^9$ and $R^{10}$ are each independently H or $C_1-C_6$ alkyl;

X is S, O, $NR^6$, $-CH=CH-$, $-CH=N-$ or $-N=CH-$;

Y is CH or N;

Z is H, O-allyl, O-phenyl, $O-CH_2CH_2CH_2OH$, S-methyl, S-propyl, S-octyl, or S-benzyl;

n is now one or two;

m is an integer ranging from one to five;

r is an integer ranging from one to five, the moiety $(CH_2)_{r}$ optionally including one or more carbon-carbon double or triple bond when r is an integer of from two to five;

t is an integer ranging from zero to five, each moiety $(CH_2)_t$ optionally including one or more carbon-carbon double or triple bond when t is an integer of from 2 to 5;

s is an integer of from one to five, the moiety (CH$_2$)$_s$ optionally including one or more carbon-carbon double or triple bond when s is an integer of from 2 to 5; and Preferred compounds include those of formula I wherein R$^1$ is —COOH.

Other preferred compounds include those wherein r is zero, R$^2$ is phenyl and R$^3$ is H.

Other preferred compounds are those wherein X is O and Y is N.

Another preferred class of compounds comprises compounds of the formula

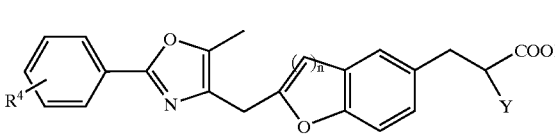

III wherein R$^4$, Y and n are as defined for formula I.

Specific preferred compounds of formula II include:

3-{4-[2-(5-Methyl-2-phenyl-oxazol-4-yl)-ethoxy]-phenyl}-2-methylsulfanyl-propionic acid;
2-Methylsulfanyl-3-[2-(5-methyl-2-m-tolyl-oxazol-4-ylmethyl)-benzofuran-5-yl]-propionic acid;
2-Benzylsulfanyl-3-[2-(5-methyl-2-phenyl-oxazol-4-ylmethyl)-benzofuran-5-yl]-propionic acid;
3-[2-(5-Methyl-2-phenyl-oxazol-4-ylmethyl)-benzofuran-5-yl]-2-octylsulfanyl-propionic acid;
3-[2-(5-Methyl-2-phenyl-oxazol-4-ylmethyl)-benzofuran-5-yl]-2-propyisulfanyl-propionic acid;
2-Allyloxy-3-[2-(5-methyl-2-phenyl-oxazol-4-ylmethyl)-benzofuran-5-yl]-propionic acid;
2-(3-Hydroxy-propoxy)-3-[2-(5-methyl-2-phenyl-oxazol-4-ylmethyl)-benzofuran-5-yl]-propionic acid;
3-[2-(5-Methyl-2-phenyl-oxazol-4-ylmethyl)-benzofuran-5-yl]-propionic acid; and
3-[2-(5-Methyl-2-phenyl-oxazol-4-ylmethyl)-benzofuran-5-yl]-2-phenoxy-propionic acid.

In one embodiment, the method of the invention relates to the treatment of cancer such as brain, squamous cell, bladder, gastric, pancreatic, breast, head, neck, oesophageal, prostate, colorectal, lung, renal, gynecological (such as ovarian) or thyroid cancer. In another embodiment, said method relates to the treatment of a non-cancerous hyperproliferative disorder such as benign hyperplasia of the skin (e.g., psoriasis) or prostate (e.g., benign prostatic hypertropy (BPH)).

The invention also relates to a method for the treatment of a hyperproliferative disorder in a mammal which comprises administering to said mammal a therapeutically effective amount of a compound of formula I or a pharmaceutically acceptable salt or hydrate thereof, in combination with an anti-tumor agent selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, and anti-androgens.

The invention also relates to a method of treating pancreatitis or kidney disease in a mammal which comprises administering to said mammal a therapeutically effective amount of a compound of formula I or a pharmaceutically acceptable salt or hydrate thereof.

The invention also relates to a method of preventing blastocyte implantation in a mammal which comprises administering to said mammal a therapeutically effective amount of a compound of formula I or a pharmaceutically acceptable salt or hydrate thereof.

The invention also relates to a method of treating diseases related to vasculogenesis or angiogenesis in a mammal which comprises administering to said mammal an effective amount of a compound of formula I or a pharmaceutically acceptable salt or hydrate thereof. In one embodiment, said method is for treating a disease selected from the group consisting of tumor angiogenesis, chronic inflammatory disease such as rheumatoid arthritis, atherosclerosis, skin diseases such as psoriasis, excema, and scleroderma, diabetes, diabetic retinopathy, retinopathy of prematurity, macular degeneration, hemangioma, glioma, melanoma, Kaposi's sarcoma and ovarian, breast, lung, pancreatic, prostate, colon and epidermoid cancer.

Further, the compounds of the present invention may be used as contraceptives in mammals.

Patients that can be treated with the compounds of formula I and the pharmaceutically acceptable salts and hydrates of said compounds according to the methods of this invention include, for example, patients that have been diagnosed as having psoriasis, BPH, lung cancer, bone cancer, pancreatic cancer, skin cancer, cancer of the head and neck, cutaneous or intraocular melanoma, uterine cancer, ovarian cancer, rectal cancer or cancer of the anal region, stomach cancer, colon cancer, breast cancer, gynecologic tumors (e.g., uterine sarcomas, carcinoma of the fallopian tubes, carcinoma of the endometrium, carcinoma of the cervix, carcinoma of the vagina or carcinoma of the vulva), Hodgkin's disease, cancer of the esophagus, cancer of the small intestine, cancer of the endocrine system (e.g., cancer of the thyroid, parathyroid or adrenal glands), sarcomas of soft tissues, cancer of the urethra, cancer of the penis, prostate cancer, chronic or acute leukemia, solid tumors of childhood, lymphocytic lymphonas, cancer of the bladder, cancer of the kidney or ureter (e.g., renal cell carcinoma, carcinoma of the renal pelvis), or neoplasms of the central nervous system (e.g., primary CNS lymphoma, spinal axis tumors, brain stem gliomas or pituitary adenomas).

The term "halo", as used herein, unless otherwise indicated, includes fluoro, chloro, bromo or iodo. Preferred halo groups are fluoro, chloro and bromo.

The term "alkyl", as used herein, unless otherwise indicated, includes saturated monovalent hydrocarbon radicals having straight, cyclic or branched moieties. It is understood that for cyclic moieties at least three carbon atoms are required in said alkyl group.

The term "alkenyl", as used herein, unless otherwise indicated, includes monovalent hydrocarbon radicals having at least one carbon-carbon double bond and also having straight, cyclic or branched moieties as provided above in the definition of "alkyl".

The term "alkynyl", as used herein, unless otherwise indicated, includes monovalent hydrocarbon radicals having at least one carbon-carbon triple bond and also having straight, cyclic or branched moieties as provided above in the definition of "alkyl".

The term "alkoxy", as used herein, unless otherwise indicated, includes O-alkyl groups wherein "alkyl" is as defined above.

The term "aryl", as used herein, unless otherwise indicated, includes an organic radical derived from an aromatic hydrocarbon by removal of one hydrogen, such as phenyl or naphthyl.

The term "4 to 10 membered heterocyclic", as used herein, unless otherwise indicated, includes aromatic and non-aromatic heterocyclic groups containing one or more heteroatoms each selected from O, S and N, wherein each heterocyclic group has from 4 to 10 atoms in its ring system. Non-aromatic heterocyclic groups include groups having only 4 atoms in their ring system, but aromatic heterocyclic groups must have at least 5 atoms in their ring system. An example of a 4 membered heterocyclic group is azetidinyl (derived from azetidine). An example of a 5 membered heterocyclic group is thiazolyl and an example of a 10 membered heterocyclic group is quinolinyl. Examples of non-aromatic heterocyclic groups are pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups, as derived from the compounds listed above, may be C-attached, S-attached or N-attached where such is possible. For instance, a group derived from pyrrole may be pyrrol-1-yl (N-attached) or pyrrol-3-yl (C-attached).

The phrase "pharmaceutically acceptable salt(s)", as used herein, unless otherwise indicated, includes salts of acidic or basic groups which may be present in the compounds of formula I.

The compounds of formula I that are basic in nature are capable of forming a wide variety of salts with various inorganic and organic acids. The acids that may be used to prepare pharmaceutically acceptable acid addition salts of such basic compounds of formula I are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts.

Those compounds of the formula I that are acidic in nature are capable of forming base salts with various pharmacologically acceptable cations. Examples of such salts include the alkali metal or alkaline earth metal salts and particularly, the sodium and potassium salts. Certain compounds of formula I may have asymmetric centers and therefore exist in different enantiomeric forms. This invention relates to the use of all optical isomers and stereoisomers of the compounds of formula I and mixtures thereof. The compounds of formula I may also exist as tautomers. This invention relates to the use of all such tautomers and mixtures thereof.

The subject invention also includes isotopically-labeled compounds, and the pharmaceutically acceptable salts thereof, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as $^{2}H$, $^{3}H$, $^{13}C$, $^{14}C$, $^{15}N$, $^{18}O$, $^{17}O$, $^{35}S$, $^{18}F$, and $^{36}Cl$, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of formula I of this invention and prodrugs thereof can generally be prepared by carrying out the procedures disclosed in the Schemes and/or in the Examples and Preparations below, by substituting a readily available isotopically labeled reagent for a non-isotopically labeled reagent.

This invention also encompasses pharmaceutical compositions containing, and methods of treating diseases related to vasculogenesis or angiogenesis in mammals through administration of prodrugs of, compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include, but are not limited to, the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs are also encompassed. For instance, free carboxyl groups can be derivatized as amides or alkyl esters. The amide and ester moieties may incorporate groups including, but not limited to, ether, amine and carboxylic acid functionalities. Free hydroxy groups may be derivatized using groups including, but not limited to, hemisuccinates, phosphate esters, dimethylaminoacetates, and phosphoryloxymethyloxycarbonyls, as outlined in D. Fleisher, R. Bong, B. H. Stewart, Advanced Drug Delivery Reviews (1996) 19, 115. Carbamate prodrugs of hydroxy and amino groups are also included, as are carbonate prodrugs and sulfate esters of hydroxy groups. Derivatization of hydroxy groups as (acyloxy)methyl and (acyloxy)ethyl ethers wherein the acyl group may be an alkyl ester, optionally substituted with groups including, but not limited to, ether, amine and carboxylic acid functionalities, or where the acyl group is an amino acid ester as described above, are also encompassed. Prodrugs of this type are described in R. P. Robinson et al., J. Medicinal Chemistry (1996) 39, 10.

DETAILED DESCRIPTION OF THE INVENTION

The compounds of formula I are readily prepared by the synthesis methods described in U.S. Pat. No. 5,089,514, described supra.

The in vitro activity of the compounds of formula I in inhibiting VEGF/GAG (glycosaminoglycan) binding may be measured using the assay described in U.S. Pat. No. 5,795,860, the subject matter of which is incorporated herein by reference.

Using mixed cellulose ester 96-well filter plates, 150 μL of Dulbeccos PBS (phosphate buffered saline) containing 10% ovalbumin is added. Compound (5.0 μL) is added at a final concentration of 1.8 μM. Compounds are dissolved in 8% DMSO (final DMSO concentration is 0.16%) and tested at concentrations of 32, 10, 3.2, 1.0, 0.32 and 0.10 μM. A mixture of $[^{125}I]$heparin-16-mer (4500 cpm per well), purified $VEGF_{165}$ (20 nM final concentration/well, prepared by Repligen, Inc.) and Dulbeccos PBS with 10% ovalbumin is added to the 96-well plate in a volume of 100 μL. Nonspecific binding is defined using 10 μM heparin-sodium from porcine intestinal mucosa. The assay plate is incubated for 60 minutes at room temperature, filtered using a Millipore filtration apparatus, the plastic bottom plate is removed and the filter plate is allowed to completely dry. The plate bottom is sealed with plastic plate seal and 25 μL of scintillation cocktail is added to each well. The top plate is sealed and is counted for radioactivity on a Microbeta Scintillation Counter. The assay is run in a final volume of 250 μL.

The activity of the compounds of formula I, in vivo, can be determined by the amount of inhibition of tumor growth by a test compound relative to a control. The tumor growth inhibitory effects of various compounds are measured according to the methods of Corbett T. H., et al. "Tumor Induction Relationships in Development of Transplantable Cancers of the Colon in Mice for Chemotherapy Assays, with a Note on Carcinogen Structure", *Cancer Res.*, 35, 2434–2439 (1975) and Corbett, T. H., et al., "A Mouse Colon-tumor Model for Experimental Therapy", *Cancer Chemother. Rep. (Part 2)*", 5, 169–186 (1975), with slight modifications. Tumors are induced in the flank by s.c. injection of $1\times10^6$ log phase cultured tumor cells suspended in 0.1–0.2 ml PBS. After sufficient time has elapsed for the tumors to become palpable (5–6 mm in diameter), the test animals (athymic mice) are treated with active compound (formulated by dissolution in appropriate diluent, for example water or 5% Gelucire™ 44/14 rn PBS by the intraperitoneal (ip) or oral (po) routes of administration once or twice daily for 4 to 10 consecutive days. In order to determine an anti-tumor effect, the tumor is measured in millimeters with Vernier calipers across two diameters and the tumor volume ($mm^3$) is calculated using the formula: Tumor weight=(length×[width]$^2$)/2, according to the methods of Geran, R. I., et al. "Protocols for Screening Chemical Agents and Natural Products Against Animal Tumors and Other Biological Systems", Third Edition, *Cancer Chemother. Rep.*, 3, 1–104 (1972). The flank site of tumor implantation provides reproducible dose/response effects for a variety of chemotherapeutic agents, and the method of measurement (tumor diameter) is a reliable method for assessing tumor growth rates.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered will be dependent on the subject being treated, the severity of the disorder or condition, the rate of administration and the judgement of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The active compound may be applied as a sole therapy or may involve one or more other anti-tumor substances, for example those selected from, for example, mitotic inhibitors, for example vinblastine; alkylating agents, for example cis-platin, carboplatin and cyclophosphamide; anti-metabolites, for example 5-fluorouracil, cytosine arabinoside and hydroxyurea, or, for example, one of the preferred anti-metabolites disclosed in European Patent Application No. 239362 such as N-(5-[N-(3,4-dihydro-2-methyl-4-oxoquinazolin-6-ylmethyl)-N-methylamino]-2-thenoyl)-L-glutamic acid; growth factor inhibitors; cell cycle inhibitors; intercalating antibiotics, for example adriamycin and bleomycin; enzymes, for example interferon; and anti-hormones, for example anti-estrogens such as Nolvadex™ (tamoxifen) or, for example anti-androgens such as Casodex™ (4'-cyano-3-(4-fluorophenylsulphonyl)-2-hydroxy-2-methyl-3'-(trifluoromethyl)propionanilide). Such conjoint treatment may be achieved by way of the simultaneous, sequential or separate dosing of the individual components of the treatment.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc. Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see *Remington's Pharmaceutical Sciences,* Mack Publishing Company, Easter, Pa., 15th Edition (1975).

Activity data for representative compounds of formula I is provided below:

| Compound Name | IC$_{50}$ (uM) |
|---|---|
| 3-{4-[2-(5-Methyl-2-phenyl-oxazol-4-yl)-ethoxy]-phenyl}-2-methylsulfanyl-propionic acid | 4.5 |
| 2-Methylsulfanyl-3-[2-(5-methyl-2-m-tolyl-oxazol-4-ylmethyl)-benzofuran-5-yl]-propionic acid | 8.0 |
| 2-Benzylsulfanyl-3-[2-(5-methyl-2-phenyl-oxazol-4-ylmethyl)-benzofuran-5-yl]-propionic acid | 2.6 |
| 3-[2-(5-Methyl-2-phenyl-oxazol-4-ylmethyl)-benzofuran-5-yl]-2-octylsulfanyl-propionic acid | 0.8 |
| 3-[2-(5-Methyl-2-phenyl-oxazol-4-ylmethyl)-benzofuran-5-yl]-2-propylsulfanyl-propionic acid | 1.5 |
| 2-Allyloxy-3-[2-(5-methyl-2-phenyl-oxazol-4-ylmethyl)-benzofuran-5-yl]-propionic acid | 13 |
| 2-(3-Hydorxy-propoxy)-3-[2-(5-methyl-2-phenyl-oxazol-4-ylmethyl)-benzofuran-5-yl]-propionic acid | 14 |
| 3-[2-(5-Methyl-2-phenyl-oxazol-4-ylmethyl)-benzofuran-5-yl]-propionic acid | 6.8 |
| 3-[2-(5-Methyl-2-phenyl-oxazol-4-ylmethyl)-benzofuran-5-yl]-2-phenoxy-propionic acid | 2.0 |

What is claimed is:

1. A method of treating cancer susceptible to compounds of the following formula, in mammals in need of such treatment, comprising administering to said mammal a therapeutically effective amount of a compound of the formula:

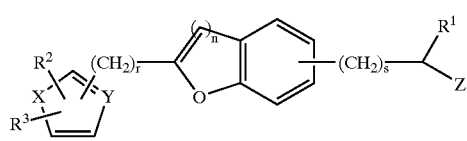

I or a pharmaceutically acceptable salt, or hydrate, wherein:
$R^1$ is —COY$^1$ wherein Y$^1$ is hydroxy, (C$_1$–C$_3$)alkoxy, phenoxy, benzyloxy, amino, (C$_1$–C$_4$)alkanoylamino, (C$_1$–C$_4$)alkanesulfonylamino, benzenesulfonylamino, naphthalenesulfonylamino, di[(C$_1$–C$_4$)] aminosulfonylamino or one of the foregoing groups mono- or disubstituted with (C$_1$–C$_3$)alkyl, trifluoromethyl, hydroxy, (C$_1$–C$_3$)alkoxy, fluoro or chloro;

$R^2$ and $R^3$ are independently selected from hydrogen, (C$_1$–C$_{10}$)alkyl, and phenyl;

X is O;

Y is N;

Z is S-methyl, S-propyl or S-octyl;

n is one;

r is an integer ranging from one to five, the moiety (CH$_2$)$_r$ optionally including one or more carbon-carbon double or triple bond when r is an integer of from two to five; and s is an integer of from one to five, the moiety (CH$_2$)$_s$ optionally including one or more carbon-carbon double or triple bond when s is an integer of from 2 to 5.

2. The method of claim 1, wherein R$^1$ is —COOH.

3. The method of claim 1, wherein r is zero, R$^2$ is phenyl and R$^3$ is H.

4. The method of claim 1, wherein the compound of formula I is a compound of the formula:

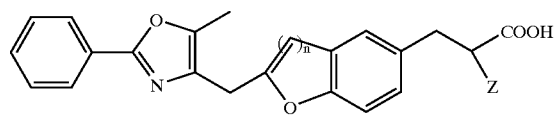

III wherein Z and n are as defined for formula I.

5. The method of claim 4, wherein the compound of formula III is selected from:

3-[2-(5-Methyl-2-phenyl-oxazol-4-ylmethyl)-benzofuran-5-yl]-2-octylsulfanyl-propionic acid;

3-[2-(5-Methyl-2-phenyl-oxazol-4-ylmethyl)-benzofuran-5-yl]-2-propylsulfanyl-proponic acid.

6. A method of treating cancer in mammals in need of such treatment, comprising administering to said mammal a therapeutically effective amount of 3-[2-(5-Methyl-2-phenyl-oxazol-4-ylmethyl)-benzofuran-5-yl]-2-octylsulfanyl-propionic acid or a pharmaceutically acceptable salt, or hydrate thereof, wherein said cancer is brain, squamous cell, bladder, gastric, pancreatic, breast, head, neck, oesophageal, prostate, colorectal, lung, renal, gynecological or thyroid cancer.

\* \* \* \* \*